United States Patent
Keith et al.

(10) Patent No.: US 7,060,059 B2
(45) Date of Patent: Jun. 13, 2006

(54) SYSTEM AND METHOD FOR INITIATING AND MAINTAINING CONTINUOUS, LONG-TERM CONTROL OF A CONCENTRATION OF A SUBSTANCE IN A PATIENT USING A FEEDBACK OR MODEL-BASED CONTROLLER COUPLED TO A SINGLE-NEEDLE OR MULTI-NEEDLE INTRADERMAL (ID) DELIVERY DEVICE

(75) Inventors: Steven Keith, Chapel Hill, NC (US); Robert S. Parker, Pittsburgh, PA (US); Noel G. Harvey, Efland, NC (US); Ronald J. Pettis, Cary, NC (US); John D. DeNuzzio, Chapel Hill, NC (US); Glenn Vonk, Fuquay-Varina, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/683,466

(22) Filed: Oct. 14, 2003

(65) Prior Publication Data

US 2004/0152622 A1    Aug. 5, 2004

Related U.S. Application Data

(60) Provisional application No. 60/417,559, filed on Oct. 11, 2002, provisional application No. 60/432,233, filed on Dec. 11, 2002.

(51) Int. Cl.
*A61M 31/00* (2006.01)
(52) U.S. Cl. .......................... 604/504; 604/67
(58) Field of Classification Search ............ 604/27, 604/31, 65–67, 503, 504, 890.1, 506, 272
See application file for complete search history.

(56) References Cited

U.S. PATENT DOCUMENTS

| | | | |
|---|---|---|---|
| 4,475,901 A | 10/1984 | Kraegen et al. | 604/67 |
| 4,494,950 A | 1/1985 | Fischell | 604/66 |
| 4,559,037 A * | 12/1985 | Franetzki et al. | 604/151 |
| 5,250,023 A | 10/1993 | Lee et al. | 604/20 |
| 5,558,640 A | 9/1996 | Pfeiler et al. | 604/67 |

(Continued)

FOREIGN PATENT DOCUMENTS

EP    1048264    11/2000

(Continued)

OTHER PUBLICATIONS

Kan, Shugen; Onodera, Hisashi; Nagayama, Satoshi; Furutani, Eiko; Araki, Mituhiko; and Imamura, Masayuki. "How to Control Blood Glucose Under Continuous Glucose Challenge", *ASAIO Journal 2003*, pp. 237-242.

(Continued)

Primary Examiner—Sharon Kennedy
(74) Attorney, Agent, or Firm—Alan W. Fiedler

(57) ABSTRACT

A closed loop therapy system for controlling a concentration of a substance, such as blood glucose concentration, in the body of a user. The system and method employ a sensor system that measures a glucose level in the body, a controller that uses the measured glucose levels to generate an output that can be used to automatically or manually control an intradermal insulin infusion system to set a constant or time-varying profile of target blood glucose concentrations in a user, and then infuse an appropriate amount of insulin into the body of the user so as to reach and maintain the target values of the blood glucose concentration.

51 Claims, 13 Drawing Sheets

Feedback Control Loop for Glucose

U.S. PATENT DOCUMENTS

| | | | |
|---|---|---|---|
| 5,569,186 A | 10/1996 | Lord et al. | 604/67 |
| 5,800,420 A | 9/1998 | Gross et al. | 604/890.1 |
| 5,860,957 A | 1/1999 | Jacobsen et al. | |
| 5,879,326 A | 3/1999 | Godshall et al. | 604/506 |
| 6,219,574 B1 | 4/2001 | Cormier et al. | |
| 6,230,051 B1 | 5/2001 | Cormier et al. | |
| 6,441,747 B1 | 8/2002 | Khair et al. | 340/870.16 |
| 6,537,264 B1 | 3/2003 | Cormier et al. | |
| 6,558,351 B1 | 5/2003 | Steil et al. | 604/131 |
| 6,653,091 B1* | 11/2003 | Dunn et al. | 435/14 |
| 6,669,663 B1 | 12/2003 | Thompson | |
| 6,740,072 B1 | 5/2004 | Starkweather | |
| 6,841,389 B1* | 1/2005 | Novikov et al. | 436/95 |
| 2002/0040208 A1 | 4/2002 | Flaherty et al. | |
| 2002/0095134 A1* | 7/2002 | Pettis et al. | 604/506 |
| 2003/0060753 A1 | 3/2003 | Starkweather | |
| 2003/0073609 A1* | 4/2003 | Pinkerton | 514/1 |
| 2003/0130616 A1 | 7/2003 | Steil et al. | |
| 2004/0073160 A1 | 4/2004 | Pinkerton | |
| 2004/0082934 A1* | 4/2004 | Pettis | 604/506 |

FOREIGN PATENT DOCUMENTS

| | | |
|---|---|---|
| WO | WO 97/48440 | 12/1997 |
| WO | WO9748440 A1 | 12/1997 |
| WO | WO 00/74753 | 12/2000 |
| WO | WO0074753 A1 | 12/2000 |
| WO | WO 02/02179 | 1/2002 |
| WO | WO0202179 A1 | 1/2002 |

OTHER PUBLICATIONS

Kan, Shugen; Onodera, Hisashi; Furutani, Eiko; Aung, Tun; Araki, Mituhiko; Nishimura, Haruo; Maetani, Shunzo and Imamura, Masayuki. "Novel Control System for Blood Glucose Using a Model Predictive Method" *ASAIO Journal 2000*, pp. 657-662.

Author Unknown "Investigational device mimics a pancreas, brings an artificial pancreas one step closer to reality," ADA Annual Meeting—San Francisco—Jun. 17, 2002.

Chassin L.J. et al. Closed-loop glucose control with IV glucose sampling and SC insulin infusion:Evaluation by simulation studies, EASD 37th Annual Mtg. Sep. 2001, Glasgow, UK; Abstract 221.

Chassin, L.J. et al., Simulating closed-loop glucose control: Effect of delay in glucose measurement. Diabetes (2002) 51:1606 Suppl. 2.

Clemens, A. H., Feedback Control Dynamics for Glucose Controlled Infusion System Med Prog Technol, (1979) 6: 91-98.

Dowd Je, et al., Glucose-based optimization of CHO-cell perfusion cultures. Biotechnology And Bioengineering (2001) 75 (2): 252-256.

Lehman E., et al., Insulin dosage adjustment in diabetes. Journal of Biomedical Engineering (1992) 14:243-249.

Parker, R. S., et al., A Model-Based Algorithm for Blood Glucose Control in Type I Diabetic Patients, IEEE Transactions on Biomedical Engineering, (1999) 46(2):148-157.

Parker, R. S., et al., The Intravenous Route to Blood Glucose Control, IEEE Engineering in Medicine and Biology, (2001) 65-73.

Parker, R.S., et al., Robust H-infinity Glucose Control in Diabetes Using a Physiological Model, AIChE J. (2000) 46 (12):2537-2549.

Parker, R.S., et al., Model Predictive Control for Infusion Pump Insulin Delivery, Proceedings of the IDEE Engineering in Medicine and Biology 18th Annual International Conference, (1996) paper No. 265, Amsterdam, The Netherlands.

Parker R. et al., Control-relevant modeling in drug delivery. Advances in Drug Delivery Reviews, (2001) 48: 211-228.

Hovorka, R. et al., Diabetes Technology & Therapeutics, Jun. 2004, vol. 6, No. 3, pp. 307-318, (Posted online on Jul. 5, 2004).

Shimoda, S. et al., Closed-loop subcutaneous insulin infusion algorithm with a short-acting insulin analog for long-term clinical application of a wearable artificial endocrine pancreas, Frontiers Med. Bioi. Engng (1997) 8 (3) :197-211.

Sorensen J.T., A Physiologic Model of Glucose Metabolism in Man and its Use to Design and Assess Improved Insulin Therapies for Diabetes, PhD Thesis, M.I.T. (1985).

Parker, R. S., et al., "The Intravenous Route to Blood Glucose Control", IEEE Engineering and Biology 2001, pp. 65-73.

* cited by examiner

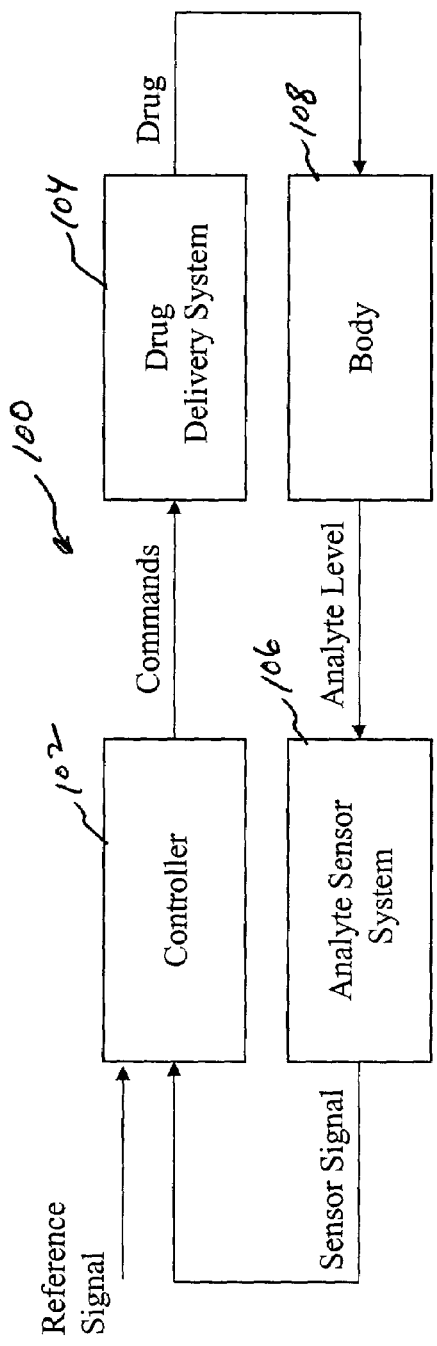
Figure 1. Generic Control Loop
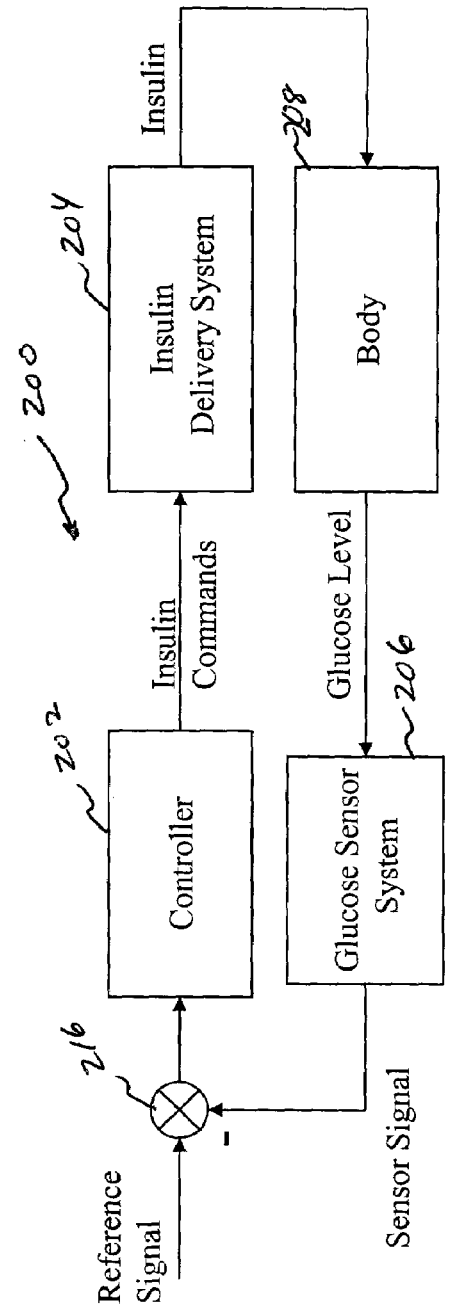
Figure 2. Feedback Control Loop for Glucose Figure 6 Model-Based Control Loop for Glucose

Examples of Potential Closed Loop Therapies

| Condition | Physiology | Therapies |
|---|---|---|
| Diabetes | Blood Glucose | Insulin |
| Respiratory | FEV1 | Inhaled Steroids Albuterol |
| Heart Failure | BP, Weight, Selected Chemistries | ACEI, Diuretic, B-Blocker, Digoxin, Coumadin, Dobutamine, BNP or ANP |
| Cancer | Tolerance, Immune Status | Various, Curative and Palliative |
| Hypertension | BP | Antihypertensives |

FIGURE 13

SYSTEM AND METHOD FOR INITIATING AND MAINTAINING CONTINUOUS, LONG-TERM CONTROL OF A CONCENTRATION OF A SUBSTANCE IN A PATIENT USING A FEEDBACK OR MODEL-BASED CONTROLLER COUPLED TO A SINGLE-NEEDLE OR MULTI-NEEDLE INTRADERMAL (ID) DELIVERY DEVICE

The present application claims benefit under 35 U.S.C. § 119(e) from Provisional Patent Application Ser. No. 60/417,559, filed on Oct. 11, 2002, and Provisional Patent Application Ser. No. 60/432,233, filed on Dec. 11, 2002, the entire contents of both provisional applications being incorporated herein by reference.

BACKGROUND OF THE INVENTION

1. Field of the Invention

The present invention relates to a system and method for maintaining continuous, long-term control of a concentration of a substance in a patient, and for determining a constant or time-varying profile of the target concentration of said substance. More particularly, the present invention relates to a system and method for maintaining continuous, long-term control of the blood glucose concentrations of a diabetic patient around a target profile using a control algorithm, for example, a feedback or model-based controller, coupled with intradermal (ID) delivery of insulin, which is preferably a short-acting insulin analog delivered via a single-needle or multi-needle array.

2. Description of the Related Art

Intradermal (ID) delivery of insulin has been recently shown to produce more rapid uptake and clearance of therapy than subcutaneous (SC) delivery of insulin, as well as increased bioavailability. This rapid onset reduces the lag time between injection (e.g., infusion commanded by a controller) and patient response.

ID delivery of insulin also avoids complications associated with intravenous (IV) delivery, and therefore, can be effectively employed in a feedback controlled insulin delivery system. A feedback control system operates to adjust a controlled variable (e.g., an insulin delivery rate or volume) based on a comparison of some measurement of a system, such as blood or tissue glucose, to a setpoint. Such a feedback control system may employ calculations encompassing the measured signal and the integral or derivative of that signal, and can thus be limited in performance by time lags associated with the system being controlled. These time lags can be due to, for example, the pharmacokinetics (PK) and pharmacodynamics (PD) of a delivered drug and its targets, any delays inherent in the measuring device, and computation time.

Therefore, it is noted that any decrease in time lags afforded by, for example, ID delivery of insulin, can result in increased performance capability of such a feedback controller. Additionally, any shortening of the therapeutic effect, for example, by way of ID delivery or the use of a short-acting insulin analog, can increase the performance of such a feedback-controlled system. Since an insulin delivery system cannot remove insulin from the patient, except by waiting for the natural PK/PD decay of activity, a shorter therapeutic time will allow for a more flexible and responsive controller.

Furthermore, certain types of patient model structures, that is, certain physiologically based models, may require that the patient undergo an insulin response test, the length of which is determined by the sampling rate and the duration of the insulin response. The use of short acting insulin reduces this time requirement relative to that required for regular insulin. Similarly, use of ID delivery of regular insulin reduces the time requirement relative to SC delivery. However, the use of intradermally delivered short-acting insulin should reduce that time even further, since both the response profile and the possible sampling intervals can be shortened.

In addition, even in non-physiologically based models, such as a 3-compartment minimal model, some insulin sensitivity parameters would preferably be generated for a patient. The duration of any such test can be shortened by use of an insulin delivery route, which provides a fast and short lived response such as that which is provided by ID delivery of short-acting insulin.

Furthermore, any feedback-controlled system for glucose will typically require a sensor to measure and transmit glucose concentrations. This sensor could measure arterial, venous or interstitial fluid concentrations, and might be located on an arm or a leg. There are thus potential inherent delays between arterial glucose and sensed glucose concentrations, which can range up to 30–40 minutes. A control system operating with a shorter sampling interval will be able to tolerate more delays in the sensor. Sensor delays may also be temporary, such as those caused by a momentary interruption in communications, accidental contact with or dislodging of the sensor, and so on. A more frequent interrogation of the sensor will thus allow for a more rapid identification of problems, and a more rapid return to control once problems are overcome.

There have been attempts to implement control of the blood glucose level of a diabetic patient using intravenous (IV) delivery of insulin, or SC delivery of short-acting insulin coupled with relatively long sampling intervals. IV delivery is generally problematic because of the need for an invasive implantation of a pump or delivery device in the patient. In a system that employs relatively non-invasive SC delivery with long sample intervals, control performance is reduced.

It is further noted that the three state model describing plasma glucose concentration as a function of plasma insulin and insulin concentration in a remote compartment currently exists. However, this model overestimates the effect of glucose concentration on cellular glucose uptake, and underestimates the contribution of elevated insulin levels. The result of the mis-match between observed physiological behavior and this three state model would be degraded controller performance.

In addition, the goal of a controller typically is to keep a system parameter (e.g., blood glucose) at or near a target value (e.g., 80 or 100 mg/dl). Because the blood glucose level of uncontrolled diabetics is typically much higher than the desired target level, when a controller is first applied to a new patient, there is a potentially large difference between the current glucose level and the target level. If a controller, such as a model predictive controller (MPC), is instructed to bring a patient's blood glucose from a hyperglycemic value to a typical target value in the shortest possible time, the result will be a rapid input of insulin, which may in turn result in hypoglycemia. If the MPC controller is instructed to keep the patient at the current hyperglycemic state, and then to gradually bring the target glucose down to a typical target value, the result will be a gradual input of insulin, with far less chance of hypoglycemia.

A conventional mode of initiating a controller would be to bring the patient to a glucose level near the target before control is begun. This could be done via manual insulin injection and/or manipulation of glucose intake. However, while technically simple, this approach would be time consuming for the patient and unreliable.

Examples of systems and devices generally related to the above fields of endeavor are described in U.S. Pat. Nos. 6,558,351, 6,441,747, 5,569,186, 5,558,640, 4,494,950 and 4,475,901, in published U.S. Patent Application No. US 2002.0095134 A1 (owned by Becton Dickinson and Company), in published European Patent Application No. EP 1 048 264 A1, in published International Patent Application No. WO 00/74753 A1, in published International Patent Application No. WO 02/02179, and in the following publications: Robert Parker and Francis Doyle, *Advances in Drug Delivery Reviews*, 48, pp. 211–228 (2001); Parker, R. S., Doyle, F. J., Peppas, N. A. The Intravenous Route to Blood Glucose Control *IEEE Engineering in Medicine and Biology*, pp. 65–73 (2001); Parker, R. S., Doyle, F. J., Peppas, N. A. A Model-Based Algorithm for Blood Glucose Control in Type I Diabetic Patients *IEEE Transactions on Biomedical Engineering*, 46(2), pp. 148–157 (1999); "*Investigational device mimics a pancreas, brings an artificial pancreas one step closer to reality*" ADA Annual Meeting—SAN FRANCISCO—Jun. 17, 2002 (obtained from, www.medtronics, com); The ADICOL (ADvanced Insulin COntrol using a closed Loop) Consortium (www.adicol.org); Biostator algorithm (Clemens, A. H., Feedback Control Dynamics for Glucose Controlled Infusion System *Med Prog Technol*, 6, pp. 91–98 (1979); Parker, R. S., et al., *Robust H-infinity Glucose Control in Diabetes Using a Physiological Model*, AIChE J. 46 (12), pp. 2537–2549 (2000); Shimoda, S. et al., *Closed-loop subcutaneous insulin infusion algorithm with a short-acting insulin analog for long-term clinical application of a wearable artificial endocrine pancreas*, Frontiers Med. Biol. Engng 8 (3): 197–211 (1997); Sorensen, J. T., *A Physiologic Model of Glucose Metabolism in Man and its Use to Design and Assess Improved Insulin Therapies for Diabetes*, PhD Thesis, M.I.T. (1985); Chassin, L. J. et al., *Simulating closed-loop glucose control: Effect of delay in glucose measurement. Diabetes* 51: 1606 Suppl. 2. (2002); Chassin, L. J. and Hovorka, R., *Closed-loop glucose control with IV glucose sampling and SC insulin infusion: Evaluation by simulation studies*, Diabetologia 44: 792 Suppl. 1 (2001); and R. S. Parker, F. J. Doyle III, J. E. Harting, and N. A. Peppas, *Model Predictive Control for Infusion Pump Insulin Delivery*, Proceedings of the IEEE Engineering in Medicine and Biology 18th Annual International Conference, paper no. 265, Amsterdam, The Netherlands, 1996, the entire contents of each being incorporated herein by reference.

A need therefore exists for a system and method capable of solving these problems and, in particular, for a minimally-invasive ID delivery device that can deliver insulin to a patient while minimizing the occurrence of hypoglycemia, and which can maintain desired blood glucose concentrations in the patient, while also being capable of operating at high sampling rates so that control performance is not degraded.

SUMMARY OF THE INVENTION

An object of the present invention relates to a system and method for maintaining continuous, long-term control of a concentration of a substance in a patient, and for determining the time-dependent profile of the desired concentration of said substance, said desired concentration being constant or varying with time.

Another object of the present invention is to provide a system and method for maintaining continuous, long-term control of the blood glucose concentrations of a diabetic patient using a control algorithm, and for determining the time-dependent profile of the desired glucose concentration, said desired concentration being constant or varying with time.

A further object of the present invention is to provide a system and method employing a minimally-invasive ID delivery device that can be used in conjunction with high sampling rates so that control performance is not degraded.

These and other objects are substantially achieved by providing a control system and method for controlling the concentration of a substance in a patient. The control system and method employ a delivery device, adapted to deliver a material to the patient intradermally to result in more rapid uptake of the material and more rapid clearance of the material, and a controller, adapted to determine the concentration of the substance in the patient that occurs in response to the material delivered to the patient, and to provide an output that is adaptable for use to control the delivery device to control an amount of the material delivered to the patient based on the concentration of the substance. For example, the output can be provided to the delivery device to automatically control the delivery device. Alternatively, the output can be information relating to the substance concentration in the form of a display, for example, which can be read by the patient or a user of the device, who can then manually adjust the delivery device to infuse the appropriate amount of material into the patient. In one application, the material includes short-acting insulin and the substance includes glucose, such that the controller controls the intradermal delivery of the short-acting insulin to the patent based on the concentration of glucose in the patient's tissue in response to the insulin delivery. The delivery device can comprise a single needle or a multi-needle array, adapted to deliver the material, such as short-acting insulin, to the patient intradermally. The system further includes a sensor which is adapted to detect the concentration of the substance, such as the glucose level, in the patient, and provide a signal representative of the concentration to the controller, which in turn analyzes the signal to determine the concentration of glucose as discussed above The system and method further employ a self-contained power source adapted to power the system, and an insulin storage device, adapted to store insulin as the material for delivery to the patient. The system can also be portable and wearable by the patient, and at least a portion of communications between the controller, the sensor and the delivery device includes wireless communications. The controller is further adapted to communicate with a device outside of the system to relay information between the controller and the patient, a health care provider, or both.

The controller can further employ a control model that includes a physiologically based model. The controller can further employ an algorithm to compare a pre-delivery concentration of the glucose present prior to delivery of the insulin to a target or predicted glucose concentration, and then to compare a post-delivery concentration of the glucose present after the delivery of the insulin to a target or predicted glucose concentration. The algorithm then further determines an appropriate insulin dose based on these pre-delivery and post-delivery comparisons. The controller can also adjust the model based on the comparison of the post-delivery glucose concentration and the target or pre-dicted glucose concentration. The controller can further allow for estimations of concentrations of a substance, for example, glucose, in areas of the body not explicitly measured, for example, arterial glucose based on an interstitial fluid glucose measurement (such practice is known in the art as "state estimation"). Furthermore, the controller can utilize either the measurement of the concentration of the substance or an estimate of the concentration of the substance in said comparisons to target or predicted concentrations.

The system and method can further be adapted to adjust the concentration of a substance, such as blood glucose, in a patient. The system and method employ a controller which is adapted to use a target profile of the concentration of the substance in the patient, and a delivery device, adapted to deliver a material, such as insulin, to the patient intradermally under the control of the controller to adjust the concentration of the substance to the target concentration substantially in accordance with the target profile.

BRIEF DESCRIPTION OF THE DRAWINGS

These and other objects, advantages and novel features of the invention will be more readily appreciated from the following detailed description when read in conjunction with the accompanying drawings, in which:

FIG. 2 is a block diagram of an example of an insulin delivery system employing feedback control according to an embodiment of the present invention;

FIG. 10 includes graphs which illustrate an example of control of a diabetic patient model for 3 days as performed by the control system shown in FIG. 6;

FIG. 13 is a table illustrating examples of closed loop therapies that can be performed by the system shown in FIG. 6;

DETAILED DESCRIPTION OF THE PREFERRED EMBODIMENTS

Figure 1D:
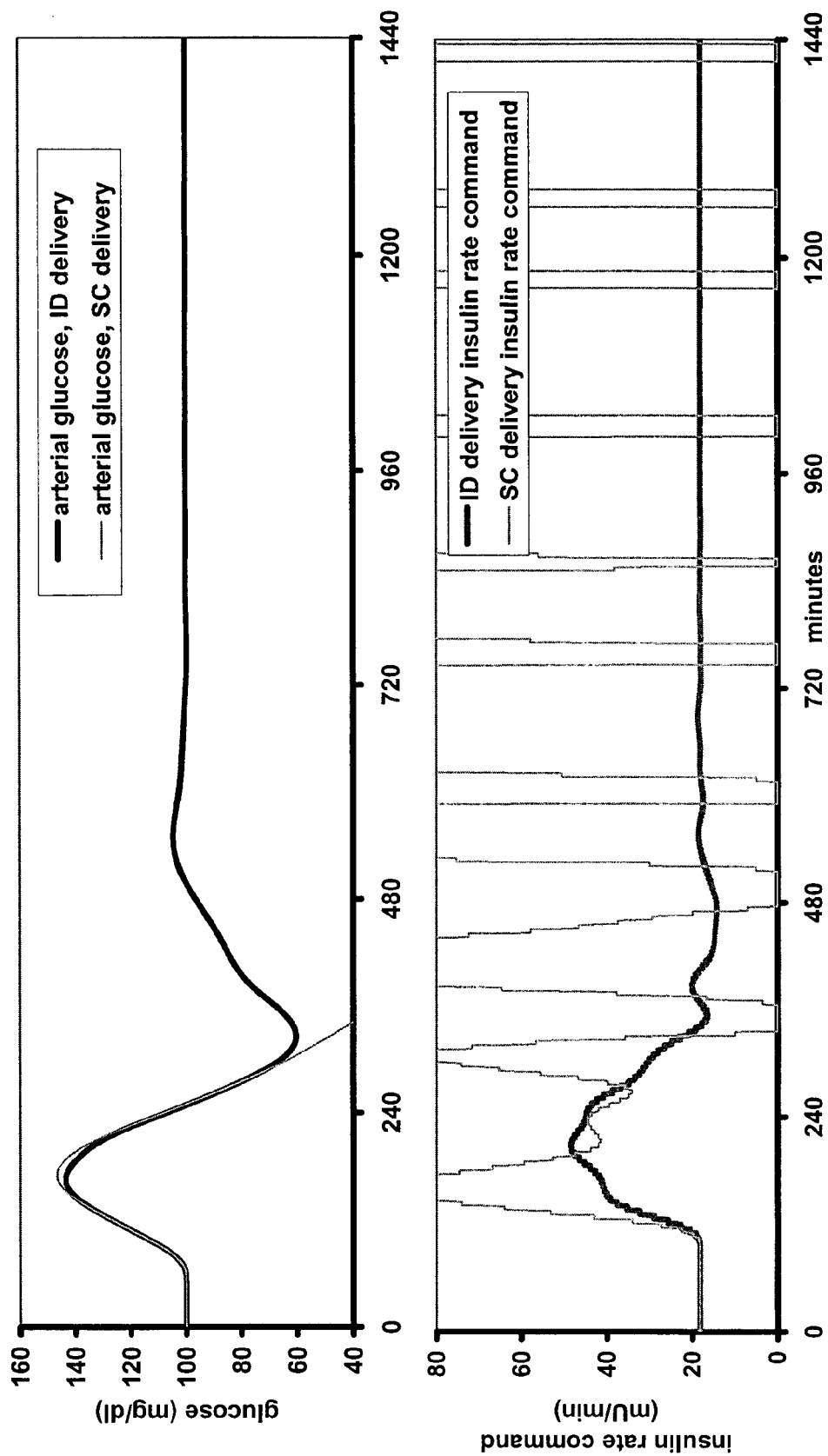
FIG. 1 is a block diagram of an example of a drug delivery system employing feedback control according to an embodiment of the present invention.

A system according to an embodiment of the invention is shown in FIGS. 1–5. As shown in FIG. 1, the system 100 can be configured generally as a drug delivery system comprising a controller 102, a drug delivery system 104 and an analyte sensor system 106. As indicated, the controller 102 provides control signals to control the drug delivery system 104 to deliver an appropriate amount of drug to a patient 108. The analyte sensor system 106 senses the level of the analyte of interest in the patient 108, and provides a sensor signal to the controller 102. Also input to the controller is a reference or set point signal which indicates the target level of the analyte. The controller 102 then can adjust the control signal accordingly to adjust the amount of drug that the drug delivery system 104 delivers to the patient 108 based on that sensor signal and the reference signal.

Figure 3:
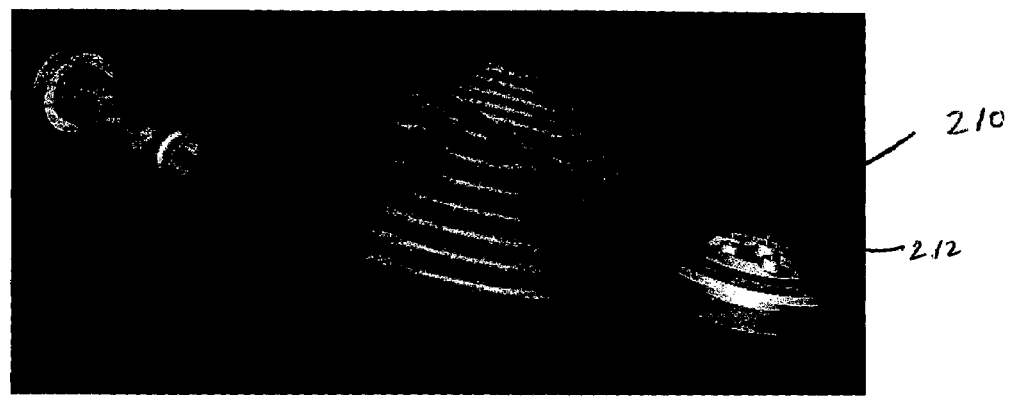
FIG. 3 illustrates an example of an insulin delivery device and sensing device employed in the system shown in FIG. 2.
Figure 4:
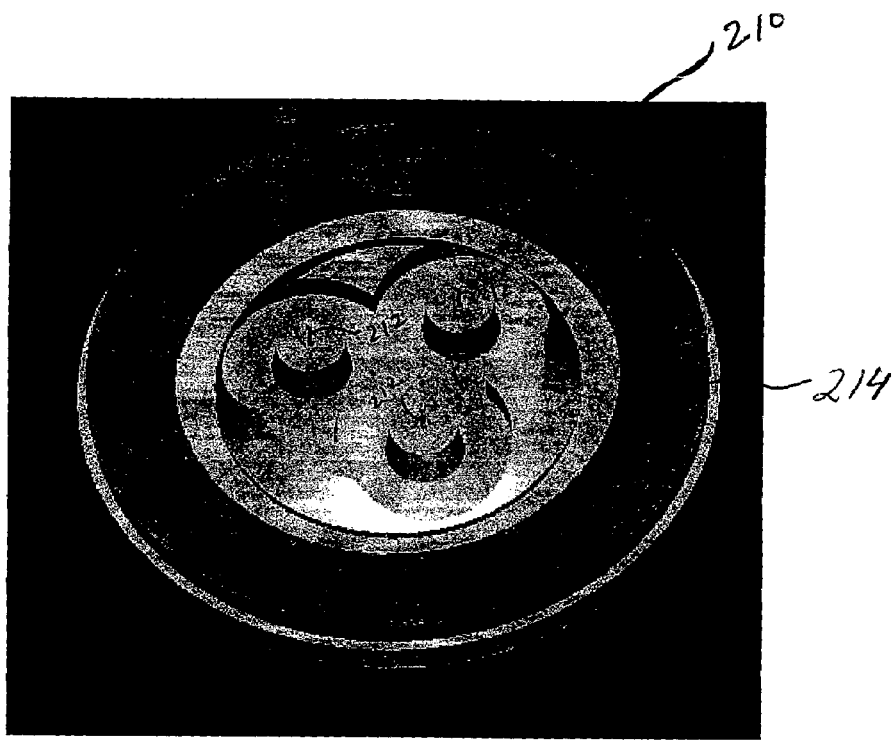
FIG. 4 is a detailed plan view of the needle array of the device shown in FIG. 3.
Figure 5:
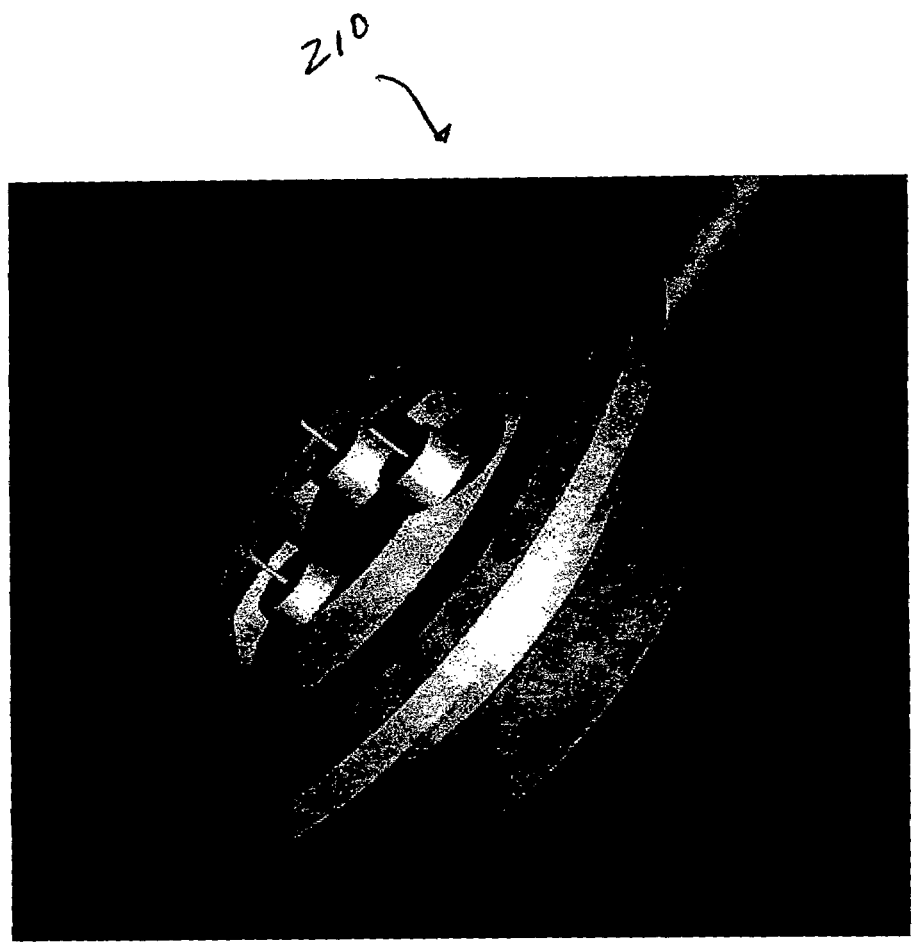
FIG. 5 is a detailed perspective view of the needle array of the device shown in FIG. 3.

As shown in FIG. 2, the system 100 can be configured within a portable, wearable closed-loop insulin delivery system 200, commonly referred to as an artificial pancreas. Similar to system 100, system 200 includes a controller 202, an insulin delivery system 204 and a glucose sensor system 206. As discussed in more detail below, the controller 202 provides control signals to control the insulin delivery system 204 to deliver an appropriate amount of insulin to a patient 208. The insulin delivery system 204 can include a needle array 210 as shown in FIGS. 3–5. Specifically, the needle array 210 includes a plurality of needles 212, each having a diameter and length sufficient to deliver insulin to the patient 208 intradermally (ID delivery). For example, each needle can have a length within the range of at or about 0.3 mm to at or about 3.0 mm, and can have a diameter within a range of at or about 30 gauge to at or about 50 gauge.

As can be appreciated by one skilled in the art, microneedles include structures with a diameter equivalent to or smaller than about 30 gauge, and typically about 30–50 gauge when such structures are cylindrical in nature. Non-cylindrical structures encompassed by the term microneedles would therefore be of comparable diameter and can include pyramidal, rectangular, octagonal, wedge, and other suitable geometrical shapes. Examples of these devices are disclosed in U.S. Pat. No. 5,879,326 to Godshall et al., U.S. Pat. No. 5,250,023 to Lee et al., and in WO 97/48440, the entire contents of each of these documents being incorporated herein by reference. Furthermore, ID compartment refers to the tissue space consisting of the dermal layer beginning immediately below the epidermis and extending to the base of the reticular dermis. On average this tissue depth is from approximately 0.05 mm–0.15 mm to approximately 1.7–2.5 mm below the outermost skin surface. One skilled in the art will recognize that there is some variability in the absolute thickness and depth of the dermal compartment based on individual biological variability associated with age, race, body site, certain disease states, and other factors. In the examples described herein, the ranges of devices used for accessing this and similar tissue spaces can be from at or about 0.3 mm to 3 mm in total depth, and more preferably <2.5 mm, with the most preferable depth for ID Delivery being <1.7 mm.

Also, the delivery system 204 can include a single needle of this type, which may be preferable in some applications. In either configuration, ID delivery of short-acting insulin analogs produces rapid onset and higher bioavailability. That is, ID delivery performed according to the embodiments of the present invention described herein results in more rapid uptake of the drugs, for example, insulin, being infused. Furthermore, intradermal insulin delivery gives significantly faster therapeutic effect versus conventional subcutaneous therapy.

Also, one or more of the needles 212 can be configured as a sensing needle electrode. That is, the surface 214 of the circumference of the needle array 210 can be configured as a reference or control electrode, while one or more of the needles 212 are configured as a sensing electrode, to provide signals to the glucose sensor system 206 that represent the glucose concentration in the patient 208. In this arrangement, the position and orientation of each sensing needle with respect to the positions and orientations of the delivery needles should be such that the delivery of the drug, for example, insulin, does not interfere with the sensing needle's or needles' ability to accurately sense the concentration of analyte level, for example, blood glucose, in the patient 208. The glucose sensor system 206 senses the level of the analyte of interest in the patient 208, and outputs a sensor signal. In this example, the sensor signal can be provided directly to the controller 202, or combined with or compared to (e.g., is subtracted from) a reference signal at a combiner 216, and then provided to the controller 202. The controller 202 then can adjust the control signal accordingly to adjust the amount of insulin that the insulin delivery system 204 delivers to the patient 208 based on the sensor signal. Also, one or more of the needles 212 can be configured as a housing for a sensor or, in other words, a sensor capable of sensing an analyte of interest can be connected to, implanted in or made integral with one or more of the needles 212. Effective integration of sensing and delivery functions in a single device requires sufficient spatial separation such that insulin administration does not affect the local glucose concentration rendering this measurement unsuitable for estimating systemic glucose concentration.

Such a system 200 could thus embody a control algorithm in a relatively simple, easy to use device, which does not impede normal activities of the user. This control system 200 can be initially parameterized by having the patient undergo an overnight (at most) insulin response test. The insulin delivery system 204 can include an intradermal delivery system capable of storing and delivering sufficient insulin for at least one day. The glucose sensor system 200 as discussed above could alternatively be implanted for long-term continuous use, or can be configured as one of many possible short-term wearable sensors. Power requirements would be low so that battery changes would be as infrequent as possible. The system 200 can also be configured to allow for wireless communication between the controller 202, sensor system 210, and delivery system 204, and communication to the patient 208 can occur via the controller 202 (e.g., an indicator such as a display on the system 200), or via an off-line base station or personal computer (PC). The system 200 can also be configured to communicate with a health care provider and/or non-local system manager, either via a telephone (modem or wireless) or the Internet, for example.

Furthermore, although one type of sensor is discussed above, the type of sensor used within the control system 200 can be one of any available sensors, as long as it has sufficient accuracy, precision, and an appropriately short response time. Sensors with longer response lags may be acceptable, since the rapid PK/PD of said material delivered ID provides more time for sensing operations within the control cycle. Sensors with reduced accuracy at high glucose values may also be acceptable, since the controller 200 should be capable of operating to control the glucose delivery system 202 as appropriate to limit an onset of hyperglycemia in the patient 208 as well.

The embodiments of the invention discussed above are based on the concepts and principles of intradermal insulin delivery, PK/PD (pharmacokinetics and pharmacodynamics), and modern control theory. Principles of ID delivery which result in rapid onsets are employed in the system 200. The basic control principle at work is that the sampling rate of the controller 202 and the therapy onset/decay rates are rapid compared to the overall system (patient and sensor) dynamics. A second relevant model predictive control (MPC) principle is that the model embedded in the controller 202 should contain adequate information about the patient's response to control inputs (e.g., therapy), and thus a therapy with rapid onset of activity will allow more complete information to be contained within the model.

Figure 6:
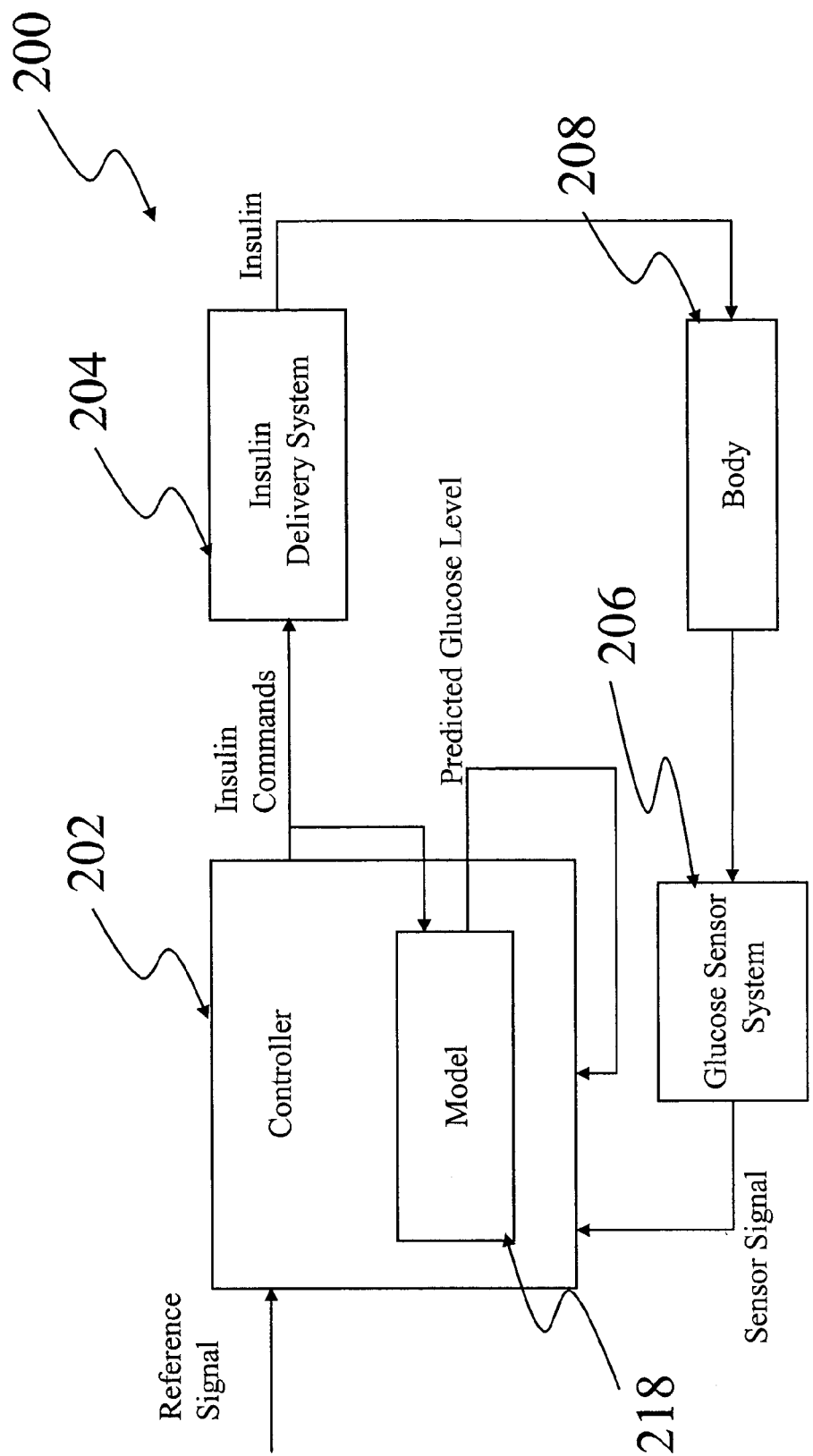
FIG. 6 is a block diagram of an example of an insulin delivery system employing model-based control, for example, a model predictive controller (MPC), according to an embodiment of the present invention.

FIG. 6 illustrates an example of the system 200 shown in FIG. 2 which further incorporates a model predictive controller (MPC) component 218 of the controller 202, the output of which can be provided to the controller 202. The sensor signal output from the sensor system 206 and the reference signal are also provided to the controller to allow calculation of the control command as discussed above with regard to FIG. 1.

As can be appreciated by one skilled in the art, a model-based or model predictive controller (MPC) contains a mathematical representation of the controlled system (patient and associated delivery and sensing devices). The controller 202 generates a control command (i.e., insulin rate or volume to be delivered) based on the current state of the patient 208 and the expected future behavior of the patient 208 (i.e., a model response). For each proceeding control step, the patient response is compared to the modeled response, and control commands are adjusted accordingly. A preferred requirement for a MPC is that the embedded model accurately reflects the system's response to control inputs. In the case of insulin delivery to a diabetic, the model reflects the patient's glucose profile in response to insulin delivery.

Depending on the type of model used, the model response can be generated by individualized testing of patients or by application of population-derived parameters (i.e., insulin sensitivity). In the system 200, the model can be constructed via individualized testing by, for example, an overnight insulin response test. An inclusive but not exhaustive list of model types includes: physiology-based, empirical (compartmental or moving average or autoregressive plus moving average), data based, neural networks, or a combination of these characteristics.

As further discussed above, the control system 200 uses ID delivery of insulin, in particular, a short-acting insulin analog, in a physiologically-based MPC application. As will be demonstrated below, simulations suggest that short acting insulin, when delivered via the ID route, allows for much better control of a diabetic patient than subcutaneous SC application of regular or short-acting insulin or ID application of regular insulin. Model based control using short-acting insulin analogs also allows for more frequent updating of the controller 202 and thus more frequent application of insulin, more accurate model construction (because the time span of insulin activity is short relative to the memory size and computational requirements of the controller), and more aggressive tuning of the controller 202 for a given model and sample time (the controller 202 attempts to return glucose concentrations to a baseline value in a shorter period of time). This yields a faster return to normal baseline, which will improve the health of the patient, and smaller instantaneous insulin volume delivered which may improve bioavailability of delivered insulin. Furthermore, smaller insulin rate commands, and smaller rate command variations, which will improve reliability and longevity of the delivery device, are also realized, along with reduced occurrence of hypoglycemia, in terms of both minimum glucose excursions and time below any threshold value, which will minimize the risk of adverse conditions for the patient.

Figure 7:
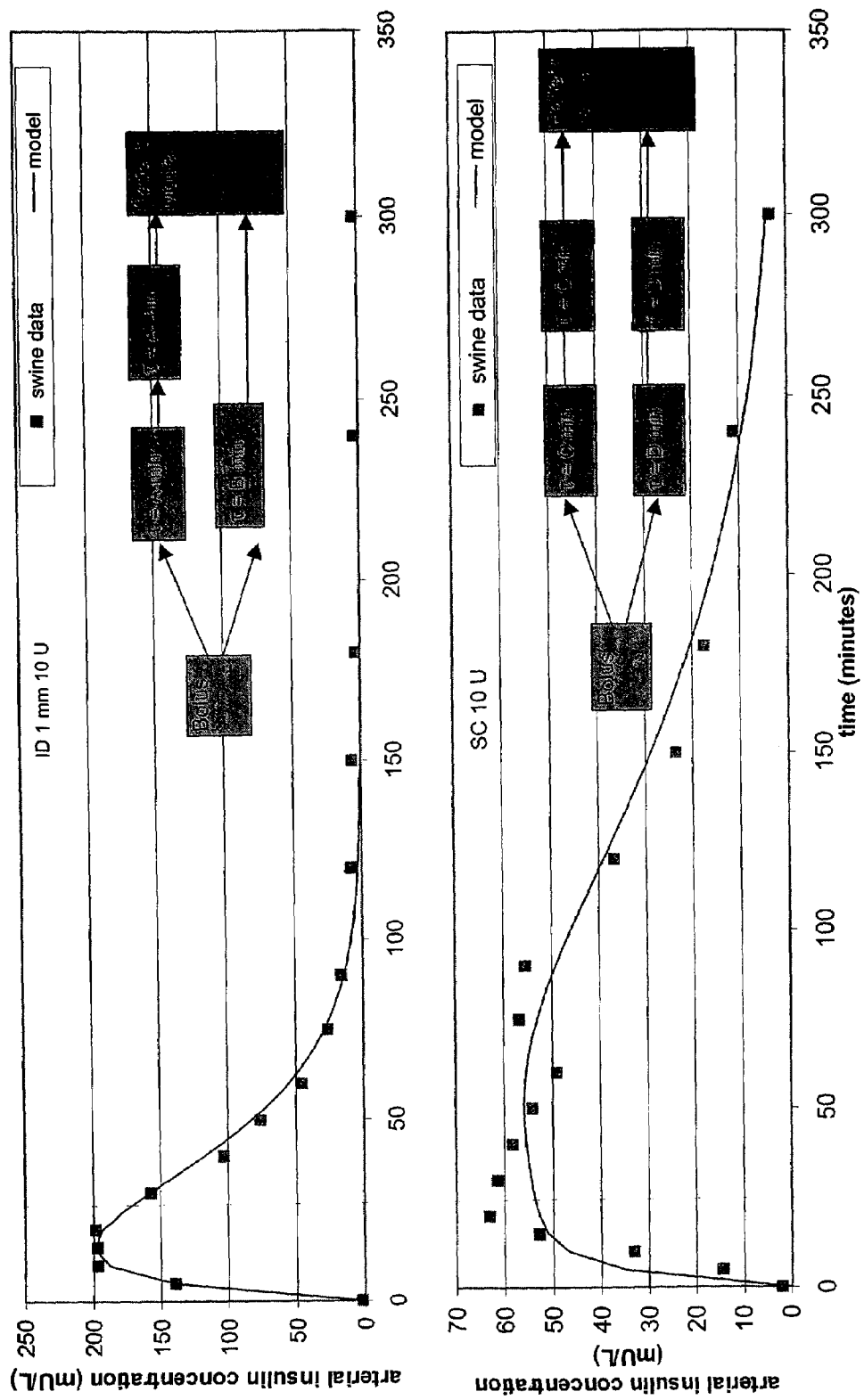
FIG. 7 includes graphs representing sample response curves attained by models that are able to replicate swine insulin response profiles using subcutaneous (SC) and intradermal (ID) insulin delivery methods.

The model 218 can also employ a mathematical model which can generate insulin response curves matching those obtained from ID insulin delivery to humans and swine. The modeling procedure is based on the arts of pharmacodynamics and pharmacokinetics. An example of this modeling uses an existing physiological model to generate arterial insulin response curves, which is described in a publication by J. T. Sorensen entitled "A Physiologic Model of Glucose Metabolism in Man and its Use to Design and Assess Improved Insulin Therapies for Diabetes", PhD Thesis, M.I.T., 1985, referenced above. The model also allows for visualization of the arterial input profile which results from a particular non-arterial insulin (i.e., SC or ID) delivery. This information can then be used to simulate SC or ID inputs into a model which is most suitable for receiving arterial insulin inputs. Sample response curves are shown in FIG. 7. As indicated, the models are able to replicate swine insulin response profiles. For the two different delivery methods, SC and ID, two different model constructions are preferred, and the time constants ($\tau$) involved in each model are different. It is noted that in this example, one small hollow needle having an outlet with an exposed height between at or about 0 mm and at or about 1 mm is used. The outlet is inserted into the skin to a depth of between at or about 0.3 mm and at or about 2 mm such that the delivery of the insulin occurs at a depth between at or about 0.3 mm and at or about 2 mm.

As demonstrated in FIG. 7, the ID insulin deliver provides "improved pharmacokinetics", meaning that an enhancement of pharmacokinetic profile is achieved as measured, for example, by standard pharmacokinetic parameters such as time to maximal plasma concentration ($T_{max}$), the magnitude of maximal plasma concentration ($C_{max}$) or the time to elicit a minimally detectable blood or plasma concentration ($T_{lag}$). By enhanced absorption profile, it is meant that absorption is improved or greater as measured by such pharmacokinetic parameters. The measurement of pharmacokinetic parameters and determination of minimally effective concentrations are routinely performed in the art. Values obtained are deemed to be enhanced by comparison with a standard route of administration such as subcutaneous administration or intramuscular administration. In such comparisons, it is preferable, although not necessarily essential, that administration into the intradermal layer and administration into the reference site such as subcutaneous administration involve the same dose levels, i.e. the same amount and concentration of drug as well as the same carrier vehicle and the same rate of administration in terms of amount and volume per unit time. For example, administration of a given pharmaceutical substance into the dermis at a concentration such as 100 μg/mL and rate of 100 μL per minute over a period of 5 minutes would, preferably, be compared to administration of the same pharmaceutical substance into the subcutaneous space at the same concentration of 100 μg/mL and rate of 100 μL per minute over a period of 5 minutes. Furthermore, if said substance has $T_{max}$ of 20 minutes for intradermal delivery and 60 minutes for subcutaneous delivery, the pharmacokinetic profile is enhanced for intradermal versus subcutaneous delivery. Similar comparisons will be evident for $C_{max}$ and $T_{lag}$ to one skilled in the art. By further example, FIG. 7 shows pharmacokinetic profiles of a fast acting insulin (Eli Lilly Lispro) delivered by subcutaneous and intradermal methods in swine. Intradermal insulin delivery results in more rapid insulin uptake than subcutaneous delivery represented by reduced $T_{max}$ and $T_{lag}$, as well as increased $C_{max}$. Therefore, intradermal delivery improves insulin pharmacokinetics. Although intradermal delivery does not typically affect intrinsic biological clearance rate or mechanism, the relative systemic clearance is reduced versus subcutaneous delivery. Therefore, rapid uptake (low $T_{max}$, high $C_{max}$) is beneficial for feedback control systems. A further description of this effect is described in published International Patent Application No. WO 02/02179 referenced above.

It should also be noted that in a continuous control loop system such as that shown in FIG. 6, it can be necessary to deliver a material continuously over a wide range of rates. For example, simulations suggest that control of a Type 1 diabetic human via continuous controlled insulin delivery requires delivery rates of zero to 40–60 mUnits (mU)/min (zero to 2.4–3.6 U/hr). Animal trials suggest that 2 U/hr is a reasonable upper limit for delivery to prevent unwanted hypoglycemic rebound and still maintain control (see, e.g., FIGS. 14 and 15). With current insulin formulations (100 U per ml fluid) these delivery rates equate to from zero to about 0.34 microliters/min or about 20.4 micoliters/1 hr (about 2 U/hr). Purely Type 2 diabetic humans generally exhibit insulin resistance, or an inability to utilize insulin. These patients may therefore require higher delivery rates. In reality, most diabetic patients exhibit some degree of insulin resistance, which increases insulin requirements. Up to 1500 uL/minute of insulin solution (150 U/min at 10 uL/U) may be delivered to meet additional insulin needs of resistant diabetes patients.

Delivery of fluid to dermal tissues through a needle, e.g., a small gauge intradermal (ID) needle, can require that the delivery system build up sufficient initial pressure. This pressure is required to overcome the resistant forces within the tissue. Only once this pressure has been developed within the delivered fluid will fluid penetrate the tissue space. If sufficient pressure is present, fluid will continue to flow. Overcoming this backpressure in high flow rate situations, such as bolus delivery of insulin, is accomplished readily by many commercially available delivery systems. However, overcoming this pressure in low and variable flow rate situations has not previously been addressed.

An advantage can be gained by using more dilute drug formulations. For example, insulin diluted to 20 IU/ml ("20 U") have been used in control tests of diabetic swine. This dilution translates to a 5-fold increase in fluid volume for a given dosage rate. The increased volume generates higher pressures needed to overcome resistant forces within the tissues at low dosage rates.

Another advantage can be gained by the used of needles with a hole, or side-port, placed an appropriate distance from the needle tip. For example, a 34G needle sized to penetrate the skin 1.5 mm (ID) with a side-port at 1.0 mm depth, can be used to deliver insulin to the ID space. The tissue pressure on this side-port will generally be less than at the needle tip, in part because the tissue at the needle tip has been compressed by the act of needle insertion. Less pressure is therefore required to promote fluid motion into the tissue space.

A continuous flow rate can be equivalently produced by providing short bursts of high flow rate of the proper duration and spacing such as to generate the correct fluid volume delivery in a given time interval. Use of high flow rates allows generation of higher pressures within the delivery system, which overcome the tissue backpressure as discussed above. Experiments have shown that flow rates of about 4 microliters/min using U20 insulin and 10 minute delivery spacing can provide adequate control and maintain flow into ID tissue. Flow was maintained even when total volumetric delivery did not exceed 1 microliter in 10 minutes. One example of a commercially available pump that can be used to achieve these rates is the Pegasus pump, available from Instech Solomon, designed to deliver 0.4 ul pulses at about 20 psi. and flow rates from 0.01 to 15 ml/hr, or 10 to 15000 ul/hr, or 0.2 to 250 uL/min.

However, generation of the short duration high flow rate pulses will by necessity result in some cases in small total fluid volumes (e.g. 1 microliter). If the delivery system is able to absorb the small delivery volume by virtue of elasticity or compliance, then the high pressure wave generated during the pulse will not impact the tissue, and no delivery will take place. Air bubbles in the system are a source of compliance, so a system which eliminates air pocket formation will have an advantage in delivering small fluid volumes. A simple means of obtaining such a system is by providing a direct connection between the needle and the delivery tubing, i.e., by gluing the end of the tubing directly around the needle or needles. One can also construct mechanical connections which maintain constant diameter fluid pathways and eliminate "dead space" where air pockets can be trapped. Low compliance tubing, which will further enhance performance in this respect, is known to the art.

For a drug delivery system attempting to maintain high backpressures, it may be advantageous to use a single needle rather than a multi-needle array. Multi-needle arrays are advantageous for delivering large fluid volumes because the arrangement distributes that volume over a larger area of the skin. A single needle may be advantageous for low volume/low rate/variable rate deliveries because all of the system pressure is directed to a single opening.

In a control loop environment, there may also be cases where moderate flow rates (10 s of microliters/hr) would be required. Transformation of these rates into pulsed profiles could result in momentary overloading of the tissue space, depending on the higher rate chosen for the pulse structure. The algorithm chosen to generate the pulse profile should take account of the fluid absorption rates of tissues, and shape the pulse (in terms of flow rate and duration) to maintain a safe margin.

It should also be noted that a closed loop control system is but one example of a situation where continuous flow rates, which may vary from zero to tens of microliters per hour, must be provided for long periods of time. One skilled in the art of therapeutics can anticipate other drug therapies which could utilize continuous low rate delivery.

Figure 8:
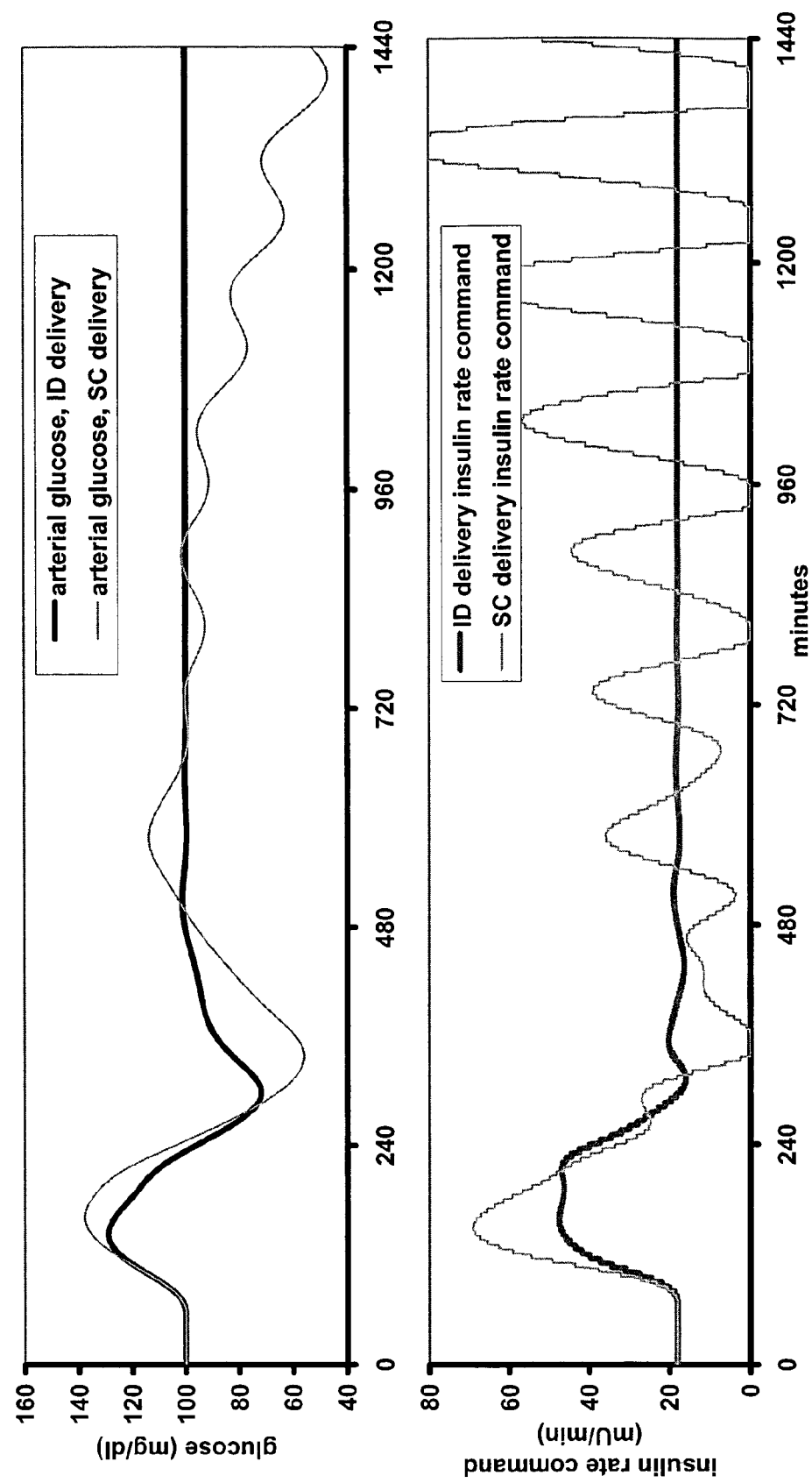
FIG. 8 include graphs which illustrate an example of control of diabetic patient model during and after a meal as performed by the control system shown in FIG. 6.

FIG. 8 includes graphs which illustrate an example of control of diabetic patient model during and after a meal. The patient model is forced with a 50 g meal, starting at 58 minutes. The controller 202 (see FIG. 2) commands either subcutaneous (SC) or intradermal (ID) delivery of Lispro to the patient 208. The sensor has an internal delay of 1 minute and a first order time constant of 1 minute. In this example the controller has a sampling interval of 5 minutes, error weighting is 3, output move weighting is 1, the number of model coefficients is 40, the move horizon is 2 and the prediction horizon is 2. The meal is based on the standard meal of Lehman and Deutsch (1992).

Figure 9:
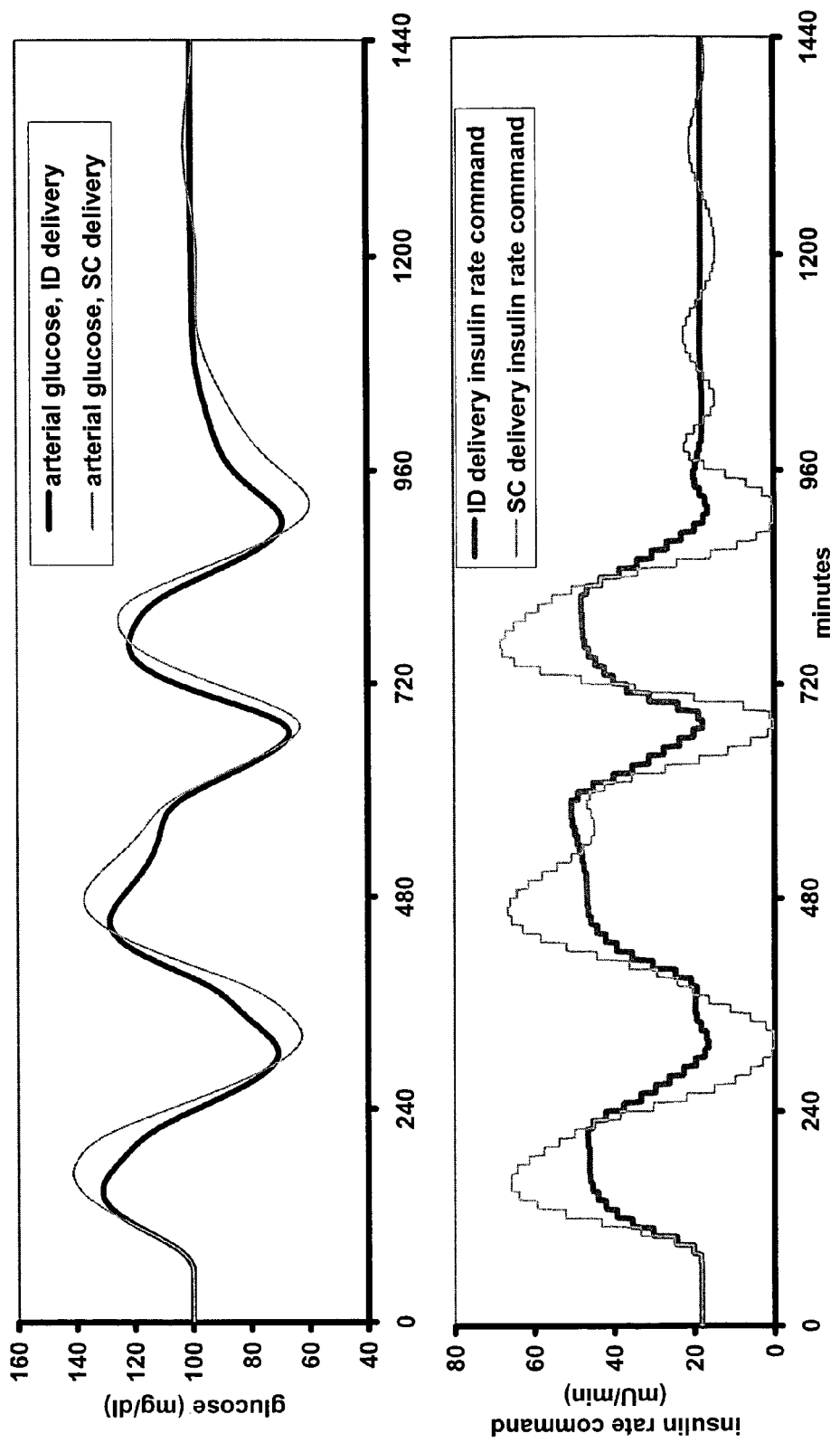
FIG. 9 includes graphs which illustrate an example of control of a diabetic patient model for 3 days as performed by the control system shown in FIG. 6.

FIG. 9 includes graphs which illustrate an example of control of a diabetic patient model for 3 meals. The patient model is forced with 50, 75, and 50 g meals. The controller 202 commands either subcutaneous (SC) or intradermal (ID) delivery of Lispro to the patient 208. The sensor has an internal delay of 1 minute and a first order time constant of 1 minute. In this example, the controller 202 has a sampling interval of 10 minutes, error weighting is 3, output move weighting is 1, the number of model coefficients is 40, the move horizon is 2 and the prediction horizon is 2. The meals are based on the standard meal of Lehman and Deutsch (1992).

FIG. 10 include graphs which illustrate an example of control of diabetic patient model during and after a meal. The patient model is forced with a 50 g meal, starting at 58 minutes. The controller 202 commands either subcutaneous (SC) or intradermal (ID) delivery of Lispro to the patient 208. In both cases, a 30 minute delay is added to the sensor output to simulate subcutaneous glucose measurement. The sensor has an internal first order time constant of 1 minute. In this example the controller has a sampling interval of 5 minutes, error weighting is 3, output move weighting is 1, the number of model coefficients is 40, the move horizon is 2 and the prediction horizon is 2. The meal is based on the standard meal of Lehman and Deutsch (1992).

Figure 11:
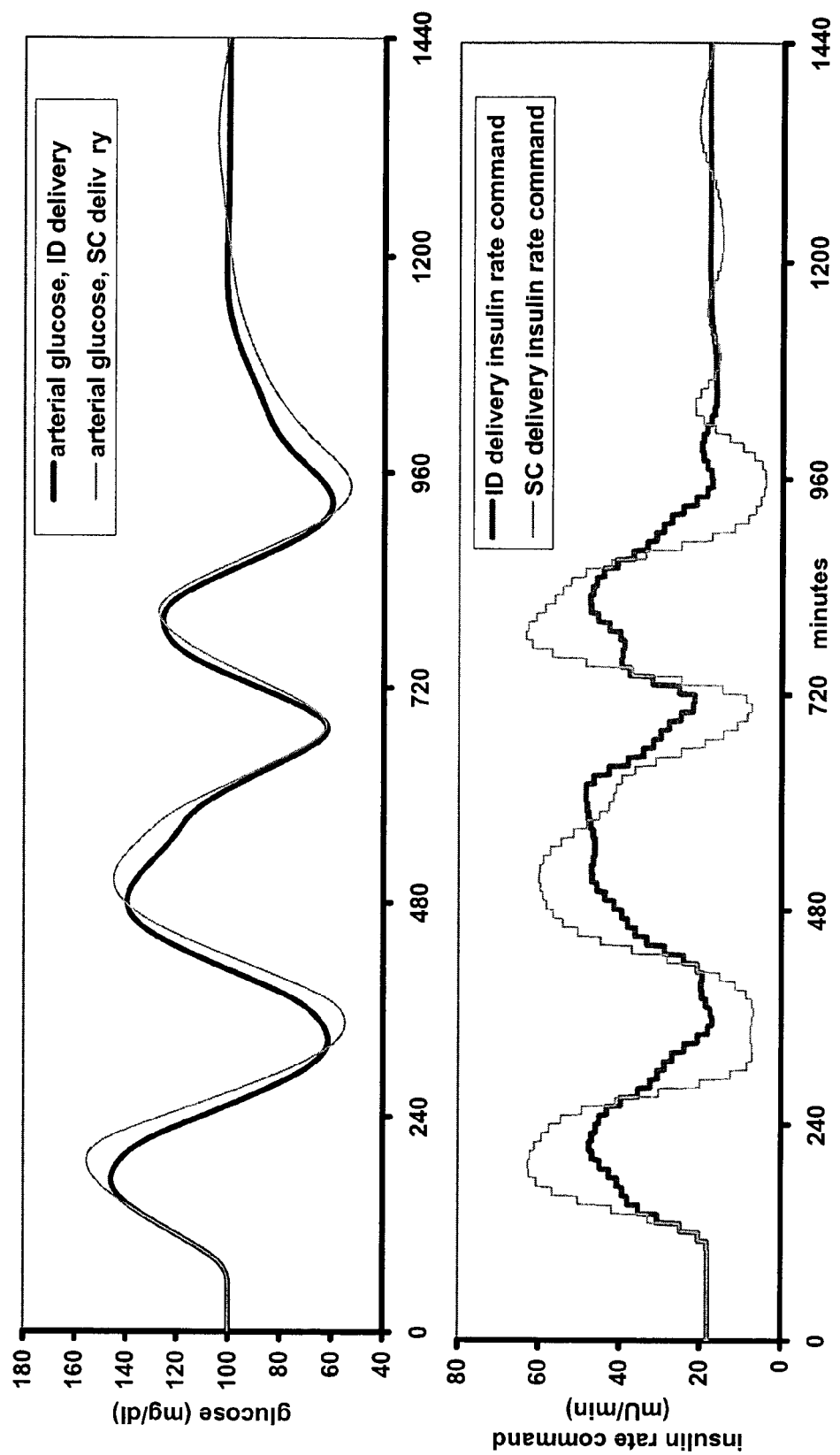
FIG. 11 includes graphs which illustrate an example of control of a diabetic patient model for 3 meals.

FIG. 11 includes graphs which illustrate an example of control of a diabetic patient model for 3 meals. The patient model is forced with 50, 75, and 50 g meals. The controller 202 commands either subcutaneous (SC) or intradermal (ID) delivery of Lispro to the patient 208. In both cases, a 30 minute delay is added to the sensor output to simulate subcutaneous glucose measurement. The sensor has an internal first order time constant of 1 minute. In this example, the controller 202 has a sampling interval of 10 minutes, error weighting is 3, output move weighting is 1, the number of model coefficients is 40, the move horizon is 2 and the prediction horizon is 2. The meals are based on the standard meal of Lehman and Deutsch (1992).

Figure 12:
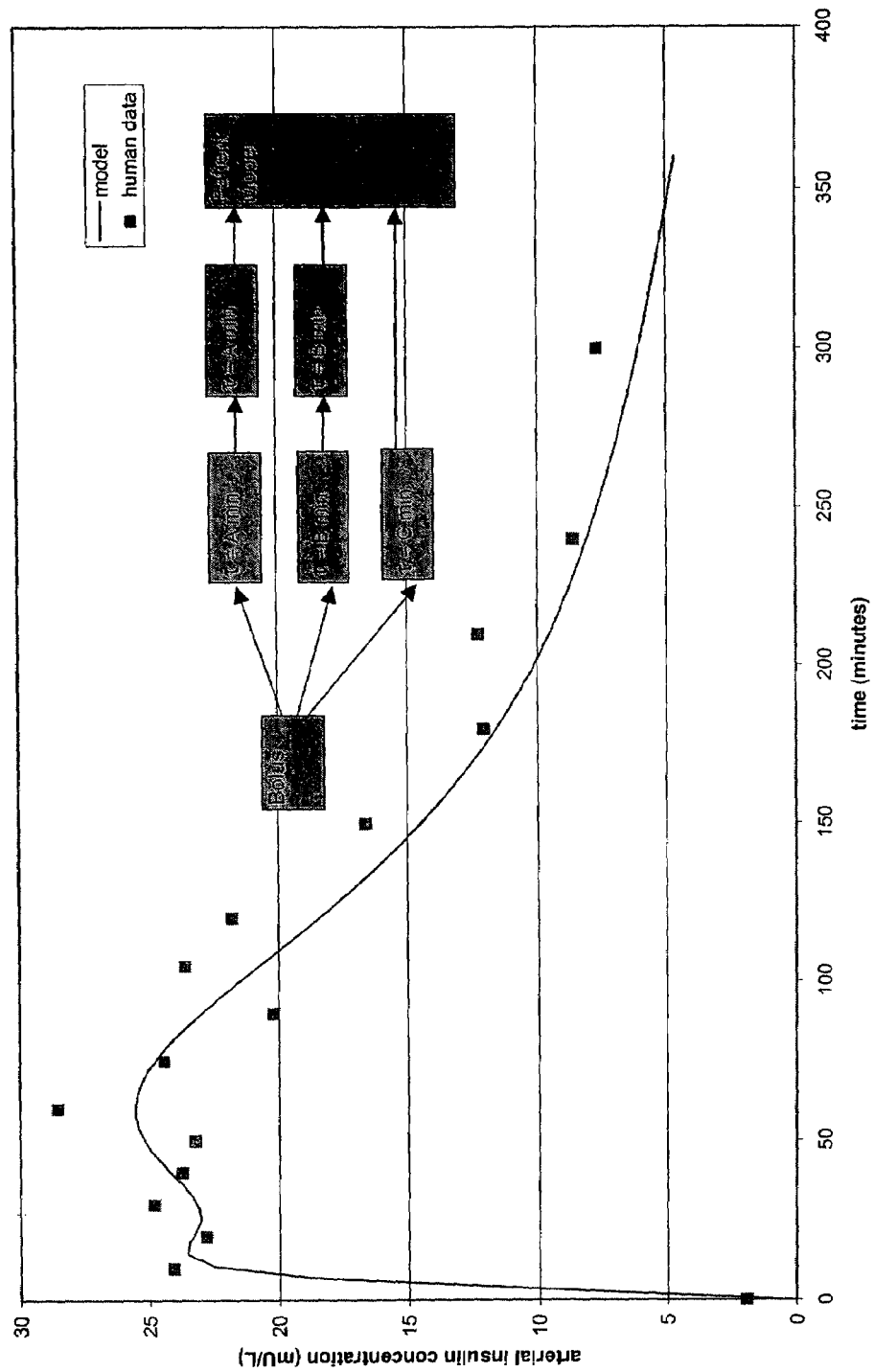
FIG. 12 include graphs which illustrate that models are able to replicate human response profiles for insulin.

FIG. 12 include graphs which illustrate that models are able to replicate human response profiles for insulin. For modeling ID delivery, three parallel delivery routes are preferred.

FIG. 13 is a table illustrating examples of closed loop therapies that can be performed by the system shown in FIG. 6, in particular. Also, all of the systems described above can further allow for estimations of concentrations of a substance, for example, glucose, in areas of the body not explicitly measured, for example, arterial glucose based on an interstitial fluid glucose measurement (such practice is known in the art as "state estimation").

As can be appreciated from the above, the control cycle should be fast enough to provide effective physiological control. Thus, the speed and frequency of physiological measurements and the rapidity with which therapy affects physiology are important for control. For example, the combination of subcutaneous measurement and delivery in a modeled control system shows degraded performance at moderate sampling frequency. However, the embodiments described above can overcome the deficiencies of such systems and enable stable control via the use of ID delivery. Even if the limitations of subcutaneous measurement are not included in a model system, the embodiments described above enable more stable control and higher performance.

As can further be appreciated from the above, the embodiments of the invention can initiate and provide continuous insulin therapy in a diabetic patient using a closed loop system, specifically one employing a Model Based Control (MBC) or more specifically a Model Predictive Control (MPC) algorithm. A MPC algorithm evaluates, at specific time intervals, current and past glucose levels, as well as recent insulin delivery history to compute an insulin dose which will bring the patient to a target glucose level. Computation of that dose takes into account a model of the patient's pharmacodynamic (PD) response to insulin and the desired future glucose target. The embodiments of the present invention use the MPC algorithm to set the future glucose target in such a way that the controller (e.g., controller 202 shown in FIG. 6) can be initiated when the patient's blood glucose is arbitrarily far away from the target while minimizing the occurrence of hypoglycemia. More particularly, the MPC algorithm sets the target profile to include a period where the target changes from current glucose values to desired target values. The rate of change of the target value during the transition from current to desired glucose values is constant (i.e. the profile includes a ramp), but the rate of change could vary with time. A target profile with time-varying target values can be used to initiate control, to recover from periods of interrupted operation, or after extreme glucose excursions. The rates of change of the target values will depend on the PK characteristics of the patient.

The data for the target ramp can optimally be written into the controller formulation so that the entirety of the ramp is contained in the controller formulation. Thus, the controller not only has information about the value of the target concentration at the present time, but also has information about the values of the target concentrations for the entire future time interval over which it makes predictions (this time is known in the art as the "prediction horizon"). The controller can thereby calculate the therapeutic dose which minimizes the difference between the predicted and target concentrations at all time intervals within the prediction horizon. A ramp duration setting can be optimized using the same patient PD data as would be used to determine the model around which the controller is built.

The advantages attained by using a ramped target according to an embodiment of the present invention can be appreciated by comparing the ramped target technique to other techniques. An alternate mode of operation would be to set a new flat target value at each computation interval. This would be the only option if, for example, a proportional integral derivative (PID) controller were being used which is not designed to consider future target values. In MPC, the current insulin dose is computed taking into account the predicted patient response and probable future insulin dosing. If the future target value is "flat" at any computation interval, the computed present and future dosing will be different from what would be computed if the future target value is ramped. This difference could lead to a slower approach to the target than could be achieved with the ramped target.

Another alternative would be to gradually change the permissible rate of insulin delivery when control is initiated. A large difference between current blood glucose values and the target will generally cause a controller (e.g., an MPC or classic controller) to generate high rate insulin delivery commands in an effort to reach the target quickly. The ramped target results in smaller initial delivery rate commands. The controller 206 can also be instructed or programmed to limit insulin delivery to an arbitrary maximum value. If, at controller initiation, the maximum delivery rate is set to the basal rate anticipated to maintain the glucose target (or at an even lower rate), then low initial rates will again result. The limit could then gradually be ramped to a final value over time. The correct choice of delivery limits could provide the same or a similar approach to target values as does the ramped target technique, but does not explicitly take advantage of the controller's optimization abilities.

Figure 14:
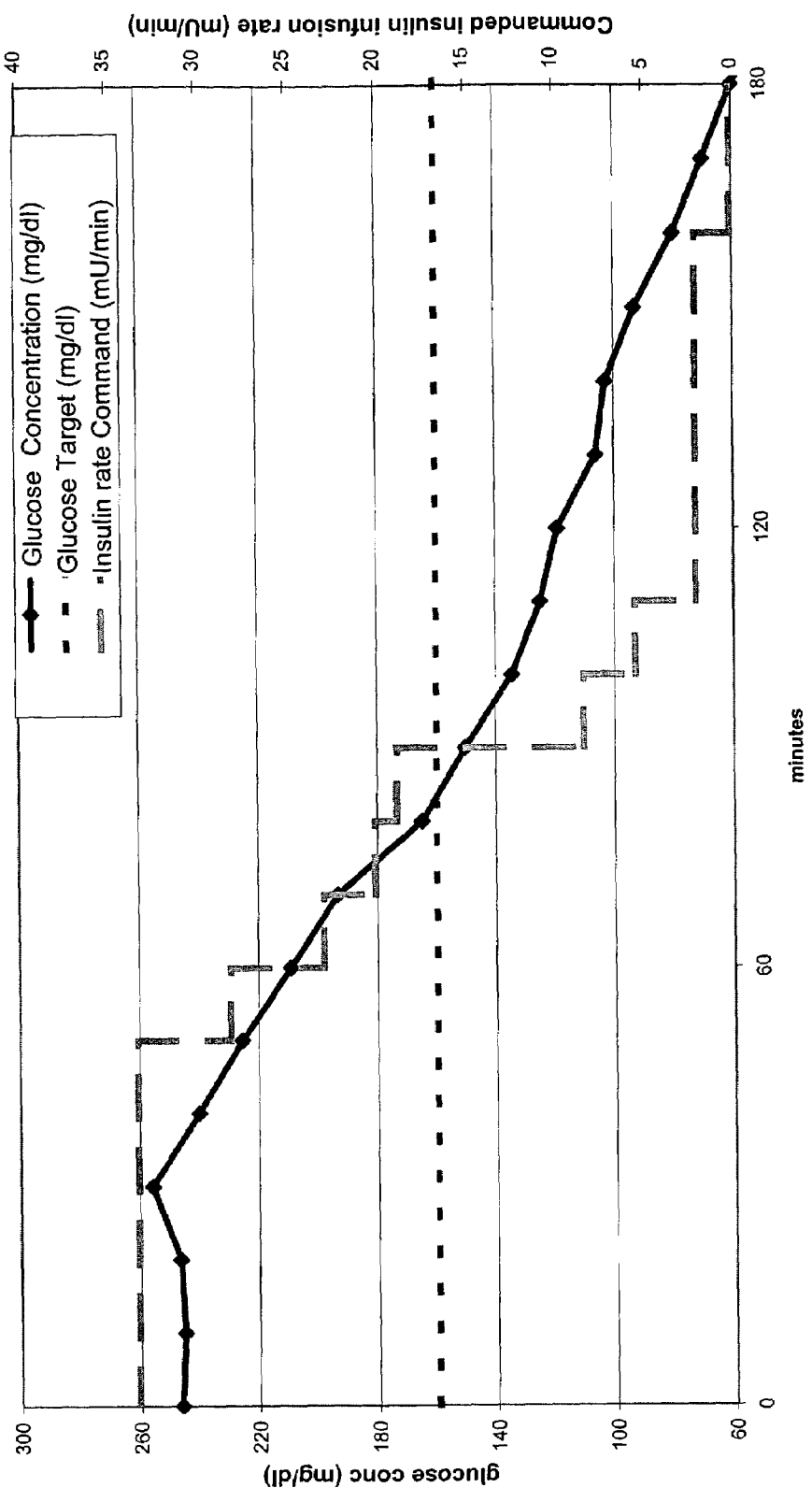
FIG. 14 is a graph illustrating an example of glucose concentration and insulin infusion rate versus time as delivered by an insulin delivery system as shown in FIG. 6, in which a flat target has been set.
Figure 15:
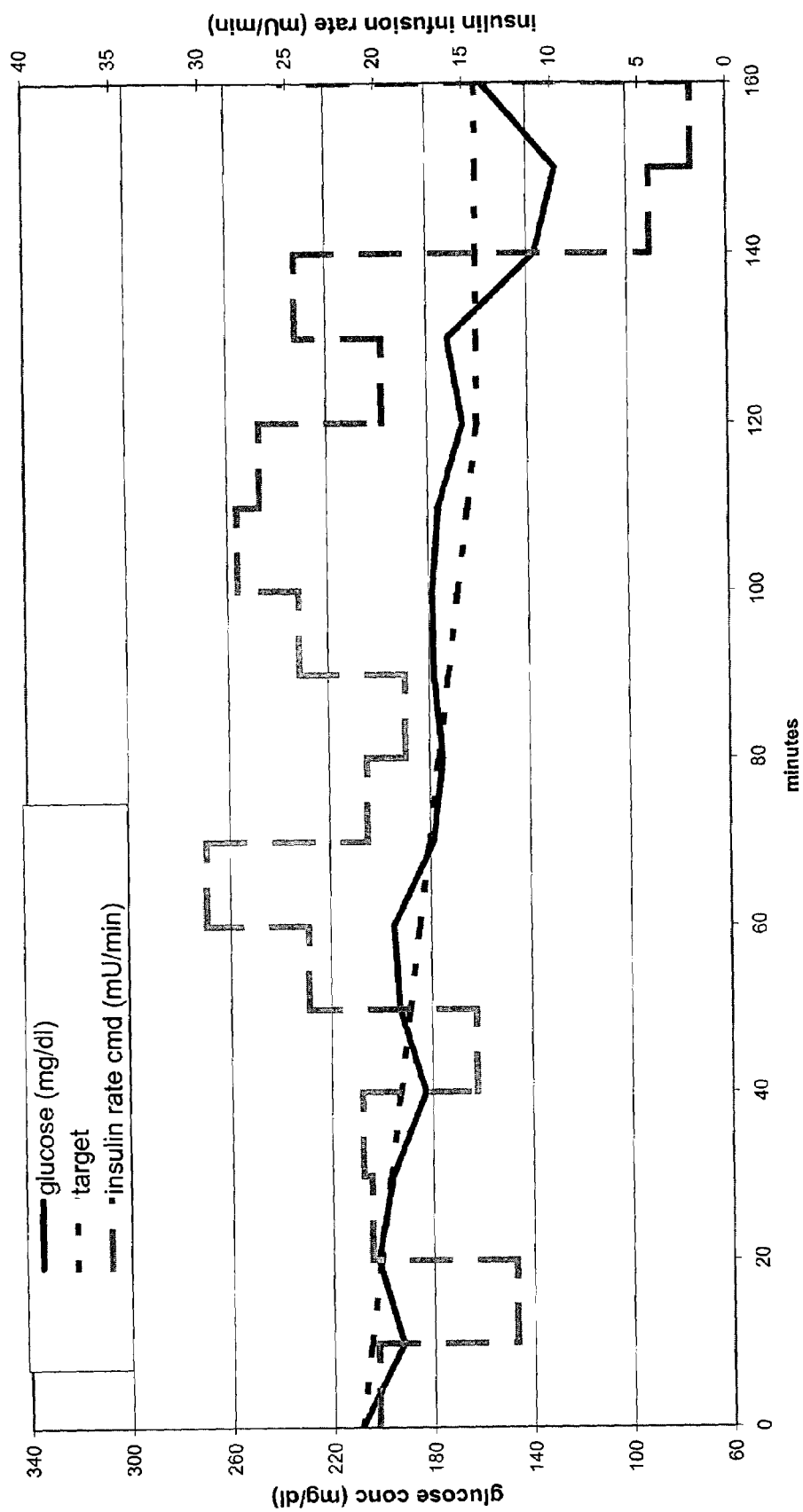
FIG. 15 is another graph illustrating an example of glucose concentration and insulin infusion rate versus time as delivered by an insulin delivery system as shown in FIG. 6, in which a ramped target has been set.

Advantages of the ramped target technique can further be appreciated from the graphs set forth in FIGS. 14 and 15. Specifically, FIG. 14 shows initiation of control with a fixed glucose target. The data are from a control experiment on a diabetic pig. Delivery was Lispro U100 through a 1.0 mm 34G needle. A controller (e.g., controller 206) is initiated with a target value of 160 mg/dl in this example. The initial glucose value was 246 mg/dl. The controller 206 generates the highest permissible delivery rates, which cause in this case a hypoglycemic episode.

FIG. 15 shows initiation of control with a ramped glucose target. The data are from a control experiment on a diabetic pig. Delivery was Lispro U100 through a triple 1.5 mm 34G needle infusor set. A controller (e.g., controller 206) is initiated with a target value equal to the initial glucose value of 209 mg/dl. The target is ramped to 160 mg/dl over two hours. The controller generates moderate delivery rates, which result in a smooth approach to the final target.

An alternative use of the embodiments of the present invention discussed above is to limit the potential for hypoglycemia after a meal. As glucose levels rise sharply after a meal, the controller (e.g., controller 206) will respond by increasing insulin delivery. A "naive" controller will ultimately keep average glucose levels at the target value, so any hyperglycemia will be followed by a period of hypoglycemia. This effect can be greatly reduced by limiting the maximum rate of insulin delivery as discussed above. Reduction of hypoglycemia can also be achieved by resetting the target value to at or near to the glucose level reached during a hyperglycemic episode. This will cause the controller 206 to significantly reduce insulin delivery rates, and thereby avoid creating hypoglycemia. Resetting of the target can be determined by, for example, analysis of recent glucose concentration data. The new target and the time allowed to return to the final target ("normoglycemia") can be determined by analysis of the patient's PD response to insulin. This same PD information will have been used to generate the original internal model in the controller 206.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system for controlling the concentration of a substance in a patient, the system comprising:
    a delivery device comprising at least one needle configured with a length sufficient to deliver a material to the intradermal compartment of said patient to result in at least one of rapid uptake of said material and rapid clearance of said material; and
    a controller, adapted to determine the concentration of said substance in the patient that occurs in response to said material delivered to the patient, and to provide an output that is adaptable for use to control the delivery device to control an amount of said material delivered to the patient based on the concentration of said substance.

2. The system of claim 1, wherein:
said controller is adapted to provide said output to said delivery device to automatically control the delivery device.

3. The system of claim 1, wherein:
said controller provides said output as information relating to the concentration of said substance which is readable for use in manual adjustment of said delivery device to infuse the appropriate amount of material into the patient.

4. The system of claim 1, wherein:
said material includes insulin and said substance includes glucose.

5. The system of claim 4, wherein:
said insulin includes short-acting insulin.

6. The system of claim 1, wherein:
said material and said substance are the same.

7. The system of claim 1, wherein:
said delivery device comprises a single-needle array or a multi-needle array, adapted to deliver said material to the patient intradermally.

8. The system of claim 1, further comprising:
a sensor, adapted to detect said concentration of said substance in the patient and to provide a signal indicative thereof to said controller, which is adapted to analyze said signal to determine the concentration of said substance in the patient.

9. The system of claim 8, wherein:
said sensor is adapted to detect said concentration of said substance at a location in said patient, and said controller is adapted to analyze said signal to estimate said concentration of said substance at another location in the patient different from said location at which said sensor detected said concentration.

10. The system of claim 1, further comprising:
a self-contained power source adapted to power said system.

11. The system of claim 1, further comprising:
an insulin storage device, adapted to store insulin as said material for delivery to said patient.

12. The system of claim 1, wherein said system is portable and wearable by the patient.

13. The system of claim 1, wherein at least a portion of communications between said controller and said delivery device includes wireless communications.

14. The system of claim 8, wherein at least a portion of communications between said controller, said sensor and said delivery device includes wireless communications.

15. The system of claim 1, wherein said controller is adapted to communicate with a device outside of the system to relay information between the controller and at least one of the patient and a health care provider.

16. The system of claim 1, wherein said controller employs a control model that includes a physiologically based model.

17. The system of claim 1, wherein said controller employs a control model that includes a data based empirical model.

18. The system of claim 1, wherein:
said material includes insulin and said substance includes glucose; and
said controller employs an algorithm to compare a pre-delivery concentration of said glucose present prior to said delivery of said insulin to a target or predicted glucose concentration, to compare a post-delivery concentration of said glucose present after said delivery of said insulin to a target or predicted glucose concentration, and to determine an appropriate insulin dose based on these comparisons.

19. The system of claim 18, wherein:
said controller employs a control model that includes a physiologically based model, and said controller adjusts said model based on the comparison of said post-delivery glucose concentration and said target or predicted glucose concentration.

20. The system of claim 18, wherein:
said controller employs a control model that includes a data based (empirical) model, and said said controller adjusts said model based on the comparison of said post-delivery glucose concentration and said target or predicted glucose concentration.

21. The system of claim 1, wherein:
said controller is adapted to provide an output that is adapted for use to control the delivery device to control an amount of said material delivered to the patient based on:
the concentration of said substance, and
an analysis of the patient's PK/PD (pharmacokinetics and pharmacodynamics) response to said material.

22. A method for controlling the concentration of a substance in a patient, the method comprising:
delivering a material to the patient intradermally to result in at lease one of rapid uptake of said material and rapid clearance of said material; and
determining the concentration of said substance in the patient that occurs in response to said material delivered to the patient; and
providing an output that is adaptable for use to control an amount of said material delivered to the patient based on the concentration of said substance.

23. The method of claim 22, wherein:
said providing provides said output to a delivery device to automatically control the delivery device to control said amount of said material delivered to the patient.

24. The method of claim 22, wherein:
said providing provides said output as information relating to the concentration of said substance which is readable for use in manual adjustment of a delivery device to infuse the appropriate amount of said material into the patient.

25. The method of claim 22, wherein:
said material includes insulin and said substance includes glucose.

26. The method of claim 25, wherein:
said insulin includes short-acting insulin.

27. The method of claim 22, wherein:
said material and said substance are the same.

28. The method of claim 22, wherein:
said delivering step includes operating a delivery device comprising a single-needle or a multi-needle array to deliver said material to the patient intradermally.

29. The method of claim 22, further comprising:
sensing said concentration of said substance in the patient and to provide a signal indicative thereof which is used in said determining step to analyze said signal to determine the concentration of said substance in the patient.

30. The method of claim 29, wherein:
said sensing senses said concentration of said substance at a location in said patient, and said determining analyzes said signal to estimate said concentration of said substance at another location in the patient different from said location at which said sensing detected said concentration.

31. The method of claim 22, further comprising:
providing power to a system that is adapted to perform said delivering, determining and providing steps using a self-contained power source.

32. The method of claim 22, further comprising:
storing insulin as said material for delivery to said patient.

33. The method of claim 22, wherein:
said delivering, determining and providing steps are performed by a system that is portable and wearable by the patient.

34. The method of claim 22, further comprising:
communicating wirelessly between a delivery device that performs said delivering step and a controller that performs said determining and providing steps.

35. The method of claim 22, further comprising:
communicating wirelessly between a delivery device that performs said delivering step, a controller that performs said determining and providing steps and a sensor that performs said sensing step.

36. The method of claim 22, further comprising:
communicating with a device outside of the system that performs said delivering, determining and providing steps to relay information between the system and at least one of the patient and a health care provider.

37. The method of claim 22, wherein said determining step employs a control model that includes a physiologically based model.

38. The method of claim 22, wherein:
said material includes insulin and said substance includes glucose; and
said determining step employs an algorithm to compare a pre-delivery concentration of said glucose present prior to said delivery of said insulin to a target or predicted glucose concentration, to compare a post-delivery concentration of said glucose present after said delivery of said insulin to a target or predicted glucose concentration, and to determine an appropriate insulin dose based on these comparisons.

39. The method of claim 38, wherein:
said determining step employs a control model that includes a physiologically based model, and said controller adjusts said model based on the comparison of said post-delivery glucose concentration and said target or predicted glucose concentration.

40. The method of claim 38, wherein:
said determining step employs a control model that includes a data based (empirical) model, and said controller adjusts said model based on the comparison of said post-delivery glucose concentration and said target or predicted glucose concentration.

41. The method of claim 22, wherein:
said rapid uptake is influenced by a PK/PD (pharmacokinetics and pharmacodynamics) effect on said material.

42. A system for adjusting the concentration of a substance in a patient, the system comprising:
a controller, adapted to provide information representing a profile of target concentrations; and
a delivery device, adapted to deliver a material to the patient intradermally under the control of the controller to adjust the concentration of the substance to the target concentration substantially in accordance with the profile.

43. A system as claimed in claim 42, wherein:
the substance is blood glucose and the material includes insulin.

44. A system as claimed in claim 42, wherein:
the profile includes a plurality of target concentrations over time.

45. A system as claimed in claim 42, wherein:
the profile is representable as a line having a non-zero slope.

46. A system as claimed in claim 42, wherein:
the delivery device includes a single-needle or a multi-needle array.

47. A method for adjusting the concentration of a substance in a patient, the method comprising:
providing information representing a profile of target concentrations; and
delivering a material to the patient intradermally under the control of the controller to adjust the concentration of the substance to the target concentration substantially in accordance with the profile.

48. A method as claimed in claim 47, wherein:
the substance is blood glucose and the material includes insulin.

49. A method as claimed in claim 47, wherein:
the profile includes a plurality of target concentrations over time.

50. A method as claimed in claim 47, wherein:
the profile is representable as a line having a non-zero slope.

51. A method as claimed in claim 47, wherein:
the delivering step includes using a delivery device having a single-needle or a multi-needle array to deliver the material.

* * * * *